(12) United States Patent
Raval et al.

(10) Patent No.: US 10,639,403 B2
(45) Date of Patent: May 5, 2020

(54) MTOR INHIBITOR ELUTING MEDICAL DEVICE

(71) Applicant: SAHAJANAND MEDICAL TECHNOLOGIES PVT. LTD., Surat (IN)

(72) Inventors: Ankur Jaykumar Raval, Surat (IN); Chhaya Babubhai Engineer, Surat (IN); Vandana Bharat Patravale, Mumbai (IN)

(73) Assignee: SAHAJANAND MEDICAL TECHNOLOGIES PRIVATE LIMITED, Surat (IN)

( * ) Notice: Subject to any disclaimer, the term of this patent is extended or adjusted under 35 U.S.C. 154(b) by 0 days.

(21) Appl. No.: 14/908,251

(22) PCT Filed: Jul. 30, 2014

(86) PCT No.: PCT/IB2014/001414
§ 371 (c)(1),
(2) Date: Jan. 28, 2016

(87) PCT Pub. No.: WO2015/015278
PCT Pub. Date: Feb. 5, 2015

(65) Prior Publication Data
US 2016/0151545 A1    Jun. 2, 2016

(30) Foreign Application Priority Data

Jul. 31, 2013    (IN) .......................... 2532/MUM/2013

(51) Int. Cl.
*A61F 13/00*    (2006.01)
*A61L 31/10*    (2006.01)
(Continued)

(52) U.S. Cl.
CPC ............. *A61L 31/10* (2013.01); *A61L 31/143* (2013.01); *A61L 31/148* (2013.01); *A61L 31/16* (2013.01);
(Continued)

(58) Field of Classification Search
CPC ............................. C08L 67/04; A61L 300/416
See application file for complete search history.

(56) References Cited

U.S. PATENT DOCUMENTS

| 5,716,981 | A | 2/1998 | Hunter et al. |
| 7,297,703 | B2 | 11/2007 | Navarro et al. |

(Continued)

FOREIGN PATENT DOCUMENTS

| EP | 1787676 A1 | 5/2007 |
| IN | 62/CHE/2012 A | 2/2013 |

(Continued)

OTHER PUBLICATIONS

Kyoung Soo Jee, et al., Heparin Conjugated Polylactide as a Blood Compatible Material, Biomacromolecules 2004, vol. 5, pp. 1877-1881, received Apr. 6, 2004; Revised Manuscript received Jun. 30, 2004.

(Continued)

*Primary Examiner* — Kyle A Purdy
(74) *Attorney, Agent, or Firm* — Nixon & Vanderhye P.C.

(57) ABSTRACT

The present disclosure relates to a coated implantable medical device, comprising: a base layer comprising mTOR inhibitor, and at least one biodegradable polymer; a middle layer comprising mTOR inhibitor, and at least one biodegradable polymer; and a top layer selected from the group consisting of hydrophilic polymer, and combination of hydrophilic polymer and antioxidant, wherein the total mTOR inhibitor concentration over the medical device is in the range of 0.7 to 3.00 µg/mm2. The present disclosure (Continued)

further relates to a method of preparing a coated implantable medical device.

18 Claims, 3 Drawing Sheets

(51) Int. Cl.
*A61L 31/14* (2006.01)
*A61L 31/16* (2006.01)

(52) U.S. Cl.
CPC ... *A61L 2300/204* (2013.01); *A61L 2300/416* (2013.01); *A61L 2420/02* (2013.01); *A61L 2420/08* (2013.01)

(56) References Cited

U.S. PATENT DOCUMENTS

| | | | |
|---|---|---|---|
| 7,517,362 B2 | 4/2009 | Shanley et al. | |
| 8,435,550 B2 | 5/2013 | Cheng et al. | |
| 2004/0087516 A1* | 5/2004 | Rosenbloom | A61K 31/121 |
| | | | 514/27 |
| 2007/0212386 A1* | 9/2007 | Patravale | A61K 31/337 |
| | | | 424/422 |
| 2008/0004695 A1 | 1/2008 | Stewart et al. | |
| 2009/0324682 A1* | 12/2009 | Popowski | A61K 9/0024 |
| | | | 424/426 |
| 2010/0233236 A1* | 9/2010 | Zhao | A61K 31/337 |
| | | | 424/423 |
| 2011/0091515 A1 | 4/2011 | Zilberman et al. | |

FOREIGN PATENT DOCUMENTS

| | | |
|---|---|---|
| WO | 2008086490 A2 | 7/2008 |
| WO | 2013102842 A2 | 7/2013 |

OTHER PUBLICATIONS

Ramila D. Mandal, et al., Antithrombotic and Antiinflammatory Effect of Heparin Conjugated Poly(L-lactide) on Inflammation Induced Cyclooxygenase, Trends Biomater. Artif. Organs, 30(2), pp. 80-84 (2016), published online Sep. 14, 2016.
International Search Report, dated Dec. 1, 2014 (PCT/IB2014/001414).
David M Martin et al, Drug-eluting stents for coronary artery disease: A review, Medical Engineering & Physics, vol. 33, Issue: 2, pp. 148-163, Oct. 10, 2010, Butterworth-Heinemann, GB (p. 156, left-hand column).
Wang X et al, Controlled release of sirolimus from a multilayered PLGA stent matrix, Biomaterials, Elsevier Science Publishers BV., Barking, GB, vol. 27, No. 32, Nov. 1, 2006, pp. 5588-5595 (p. 5594, last paragraph).
Gioti M et al, Evaluation of the functionality of biodegradable polymeric platforms for drug delivery systems, Applied Surface Science, col. 281, Apr. 26, 2013, pp. 54-59 (Abstract).

* cited by examiner

MTOR INHIBITOR ELUTING MEDICAL DEVICE

BACKGROUND OF THE INVENTION

1. Technical Field

The present disclosure relates to a coated implantable medical device which results in a controlled drug release. The present disclosure further relates to a method of preparing a coated implantable medical device.

2. Related Art

Mammalian target of rapamycin (mTOR) is a serine/threonine kinase, which belongs to phosphatidylinositol-3 kinase (PI3K) related kinases (PIKKs) family. mTOR regulates cellular metabolism, growth, and proliferation, and therefore is a target for the development of a number of mTOR inhibitors.

Implantable medical devices are often used for delivery of a beneficial agent, such as a drug, to an organ or tissue in the body at a controlled delivery rate over an extended period of time. These devices may deliver agents to a wide variety of bodily systems to provide a wide variety of treatments.

One of the many implantable medical devices which have, been used for local delivery of mTOR inhibitor is the stent. Stents are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

U.S. Pat. No. 5,716,981 discloses a stent that is surface-coated with a composition comprising a polymer carrier and paclitaxel (a well-known compound that is commonly used in the treatment of cancerous tumors).

Indian Patent Application 62/CHE/2012 relates to a pharmaceutical formulation comprising of 40-O-(2-hydroxyethyl) derivative of sirolimus (Everolimus) and coating on the implantable medical devices including coronary stents.

U.S. Pat. No. 7,297,703 discloses a mixture comprising a poly-ene macrolide and an antioxidant. The poly-ene macrolide is selected from the group consisting of rapamycin, a 16-O-substituted rapamycin, and a 40-O-substituted rapamycin. The antioxidant is selected from the group consisting of vitamin B, vitamin C, 2,6-di-tert-butyl-4-methylphenol (BHT), and combinations thereof.

U.S. Pat. No. 7,517,362 relates to a therapeutic agent delivery device which comprises a gradient of therapeutic agent within mixing layers which provides for the controlled release of water soluble therapeutic agents.

U.S. Pat. No. 8,435,550 discloses a drug-delivery system comprising at least 100 μg of everolimus and clobetasol, such that the ratio of everolimus to clobetasol is at least 10:1 (w/w) or the amount of everolimus by weight is at least 10 times more than clobetasol.

US Patent Application No. 20080004695 discloses an implantable medical device comprising: a polymeric matrix disposed over the device, wherein the polymeric matrix comprises everolimus and pimecrolimus.

US Patent application No. 20110091515 describes about the porous coating containing the drug and polymers.

Of the many problems that may be addressed through stent-based local delivery of beneficial agents, one of the most important is restenosis. Restenosis is a major complication that can arise following vascular interventions such as angioplasty and the implantation of stents.

The major contributing factor for restenosis smooth muscle cell proliferation and migration. To minimize the uncontrolled cell proliferation, anti-restenosis drugs are used in the form of thin film coating over stent surface which are programmed to be released in controlled manner by incorporating polymers. The important challenge here is the control over drug release and utilization of permanent polymers. Non-degradable polymers are biocompatible; however there are clinical evidences where delayed endothelization, late stent thrombosis and local hypersensitivity issues were associated with them. Moreover, controlled drug release is required to target the biochemical mechanisms during specific time periods. Less control over release will result in high initial burst which will be non-desirable as it may have local toxic events and low drug release may not exhibit adequate anti-proliferative effect due to lower drug concentration among tissues.

SUMMARY

The present disclosure recognizes that there is a need for a drug eluting medical device which results in a controlled drug release to the target. The present disclosure relates to a coated implantable medical device, comprising: a base layer comprising mTOR inhibitor, and at least one biodegradable polymer; a middle layer comprising mTOR inhibitor, and at least one biodegradable polymer); and a top layer selected from the group consisting of hydrophilic polymer, and combination of hydrophilic polymer and antioxidant, wherein the total mTOR inhibitor concentration over the medical device is in the range of 0.7 to 3.00 μg/mm².

The present disclosure further relates to a method of preparing a coated implantable medical device.

These and other features, aspects, and advantages of the present disclosure will become better understood with reference to the following description. This statement is provided to introduce a selection of concepts in simplified form. This statement is not intended to identify key features or essential features of the subject matter, nor is it intended to be used to limit the scope of the subject matter.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components, in which.

DETAILED DESCRIPTION

Figure 1:
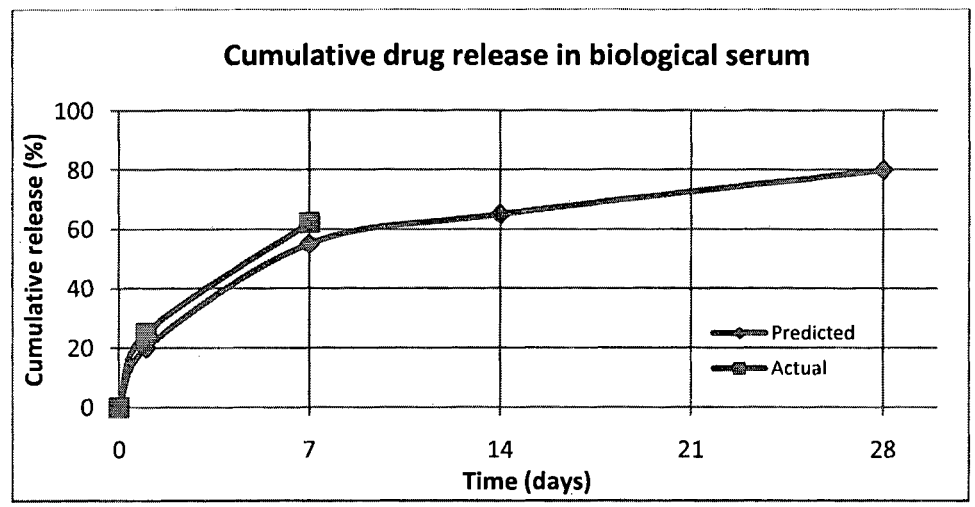
FIG. 1 illustrates the drug release profile of stents.

The present invention now will be described more fully hereinafter. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Definitions

The terms "comprise" and "comprising" are used in the inclusive, open sense, meaning that additional elements may be included. The terms will be understood to imply the inclusion of a stated element or step or group of element or steps but not the exclusion of any other element or step or group of element or steps. It is not intended to be construed as "consists of only."

An "mTOR inhibitor" as used in the present disclosure is a compound which targets intracellular mTOR ("mammalian Target of rapamycin"). mTOR is a family member of phosphatidylinositol 3-kinase (P13-kinase) related kinase. The compound rapamycin and other mTOR inhibitors inhibits mTOR activity via a complex with its intracellular receptor FKBP12 (FK506-binding protein 12). mTOR modulates translation of specific mRNAs via the regulation of the phosphorylation state of several different translation proteins, mainly 4E-PB1, P70S6K (p7056 kinase 1) and eEF2. Drug used in the present disclosure means mTOR inhibitors. Examples of mTOR inhibitors are everolimus, sirolimus, pimecrolimus, tacrolimus, zotarolimus, biolimus, rapamycin and combinations thereof.

"Medical device" refers to any type of appliance that is totally or partly introduced, surgically or medically, into a patient's body or by medical intervention into a natural orifice. The duration of implantation may be essentially permanent, i.e., intended to remain in place for the lifespan of the patient; until the device biodegrades; or until it is physically removed. The medical device used in the present disclosure includes but not limited to a stent, a catheter balloon, guide wire, heart valve, catheter, vena cava filter, vascular graft, a stent graft and combinations thereof.

"Polymer" refers to a molecule(s) composed of a plurality of repeating structural units connected by covalent chemical bonds. The polymeric matrix which is disposed over a medical device can be a biocompatible polymer that can be biostable or biodegradable and can be hydrophobic or hydrophilic.

"Antioxidant" refers to a molecule that inhibits the oxidation of other molecules. The antioxidant is within the top layer to protect mTOR inhibitors against oxidative degradation. The concentration of an antioxidant in the top layer is normally in the range of 0.5% w/w to 10% w/w.

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The "solution concentration" defines the amount of solids in the solution. The solid involves drug and polymers that are dissolved in the solution. The concentration is also one of the parameter that affects the functional attributes of drug eluting stent like release kinetics.

The present disclosure relates to a medical device, preferably stent that has been prepared by coating the bare metallic stent with blend of mTOR inhibitors with biodegradable polymers in multiple layers. mTOR inhibitors are incorporated in base layer and middle layer while top layer is coated to protect the underneath layers. The top layer does not contain any mTOR inhibitors, however, can contain antioxidant.

The stent is coated in three layers among them, base layer and middle layer has mTOR inhibitor while top layer consists of hydrophilic PVP layer with antioxidant. Total mTOR inhibitor concentration over the entire stent surface is ranges from 0.7-3.00 µg/mm². The mTOR inhibitor concentration for base layer is in the range of 0.6 to 2.2 µg/mm², while the mTOR inhibitor concentration for middle layer is in the range of 0.1 to 0.8 µg/mm². The top layer does not have any mTOR inhibitor in it.

The present disclosure relates to a coated implantable medical device, comprising: a base layer comprising mTOR inhibitor, and at least one biodegradable polymer; a middle layer comprising mTOR inhibitor, and at least one biodegradable polymer; and a top layer selected from the group consisting of hydrophilic polymer, and combination of hydrophilic polymer and antioxidant, wherein the total mTOR inhibitor concentration over the medical device is in the range of 0.7 to 3.00 µg/mm².

The present disclosure further relates to a coated implantable medical device, comprising: a base layer comprising mTOR inhibitor, at least one biodegradable polymer and an antioxidant; a middle layer comprising mTOR inhibitor, at least one biodegradable polymer, and an antioxidant; and a top layer selected from the group consisting of hydrophilic polymer, and combination of hydrophilic polymer and antioxidant, wherein the total mTOR inhibitor concentration over the medical device is in the range of 0.7 to 3.00 µg/mm².

The mTOR inhibitor used in the present disclosure is selected from the group consisting of everolimus, pimecrolimus, tacrolimus, zotarolimus, biolimus, rapamycin and combinations thereof. Everolimus is the preferred mTOR inhibitor used in the present disclosure.

The biodegradable polymer used in the present disclosure is selected from the group consisting of poly L-Lactide-caprolactone (PLCL), poly L-Lactide (PLLA), poly dl lactide (PDLLA), poly dl lactide-co-glycolide (PLGA), poly dl lactide-co-caprolactone (PLLCL), and combinations thereof. PLCL, PLLA and combinations thereof are the preferred biodegradable polymer used in the base layer and middle layer of the present disclosure. The PLLA and PLCL in the base layer and middle layer have a weight ratio of ranges from 10% to 40% based on the mTOR inhibitor weight. The co-polymer ratio of L-Lactide and caprolactone is in the range of 10:90 to 50:50 (mole %).

The hydrophilic polymer used in the present disclosure is selected from the group consisting of pyrrolidones, poly ethylene glycols and combinations thereof. Polyvinyl pyrrolidone is the preferred hydrophilic polymer used in the present disclosure.

The antioxidant used in the present disclosure is selected from the group consisting of tocopherol acetate, Vitamin E, butylated hydroxyl toluene (BHT) and combinations thereof. Tocopherol acetate is the preferred antioxidant used in the present disclosure. The antioxidant is used to protect mTOR inhibitors against oxidative degradation. 0.5 to 10% (w/w) of the antioxidant with respect to 1.1 to 10% (w/w) of the mTOR amount is used in the present disclosure. The amount of antioxidant is dependent on drug amount and not on the amount of hydrophilic polymer in the top layer.

The medical device of the present disclosure is selected from the group consisting of a stent, a catheter balloon, guide wire, heart valve, catheter, vena cava filter, vascular graft, a stent graft and combinations thereof. The medical device used in the present disclosure is a stent.

The polymer and mTOR inhibitor in the base layer and middle layer has a solution concentration in the range of 0.01 to 1% (w/v) with respect to the total solution concentration of the three layers. The polymer and mTOR inhibitor in the base layer has a solution concentration in the range of 0.1 to 1% (w/v) with respect to the total solution concentration of the three layers. The polymer and mTOR inhibitor in the middle layer has solution concentration in the range of 0.01 to 1% (w/v) with respect to the total solution concentration of the three layers.

The polymer and the antioxidant in the top layer have a solution concentration in the range of 0.01 to 5% (w/v) with respect to the total solution concentration of the three layers. The polymer and the antioxidant in the top layer have a solution concentration in the range of 0.10 to 1% (w/v) with respect to the total solution concentration of the three layers. The solution concentration defines the amount of solids in the solution. The solids involve mTOR inhibitor and polymers that are dissolved in the solution. The concentration is also one of the parameter that affects the functional attributes of mTOR inhibitor eluting medical device, preferably stent like release kinetics.

The mTOR inhibitor to the at least one biodegradable polymer in the base layer is in the range of 10:90 to 30:70 by weight. The mTOR inhibitor to the at least one biodegradable polymer in the base layer is in the range of 10:90 to 35:65 by weight. Further, the mTOR inhibitor to the at least one biodegradable in the middle layer is of 15:85 by weight.

The mTOR inhibitor to the at least one biodegradable polymer in the middle layer is in the range of 15:85 to 35:65 by weight. The mTOR inhibitor to the at least one biodegradable polymer in the middle layer is in the range of 15:85 to 40:60 by weight. The mTOR inhibitor to the at least one biodegradable polymer in the middle layer is of 23:77 by weight. The mTOR inhibitor to the at least one biodegradable polymer in the middle layer is of 25:75 by weight.

The amount of hydrophilic polymer in the top layer is in the range of 0.1 µg to 1.0 µg per unit area (in $mm^2$) of stent total surface area.

The coating process disclosed in the present disclosure is done on the abluminal surface, luminal surface and side walls of the coated implantable medical device.

An embodiment of the present disclosure discloses a coated implantable medical device, comprising: a base layer comprising everolimus and a blend of PLCL and PLLA; a middle layer comprising everolimus and a blend of PLCL and PLLA; and a top layer comprising polyvinyl pyrrolidone and tocopherol acetate, wherein the total mTOR inhibitor concentration over the medical device is in the range of 0.7 to 3.00 µg/$mm^2$.

The mTOR eluting medical device has the mTOR inhibitor dose of 0.7-3.00 µg/$mm^2$ based on the mTOR inhibitor concentration required to prevent the restenosis process. Restenosis process means recurrence of stenosis, a narrowing of a blood vessel, leading to restricted blood flow. Restenosis is a wound healing process that reduces the vessel lumen diameter by extracellular matrix deposition, neointimal hyperplasia, and vascular smooth muscle cell proliferation, and which may ultimately result in renarrowing or even reocclusion of the lumen.

The present disclosure relates to a pharmaceutical formulation comprising of mTOR inhibitor and coating of said formulation on the implantable medical devices.

The medical device was coated with three different layers by air atomized spray coating technology.

The present disclosure further relates to a method of preparing a coated implantable medical device, the process comprising: pre-cleaning the medical device using an organic solvent to obtain a cleaned medical device; and coating the cleaned medical device with a base layer comprising mTOR inhibitor, and at least one biodegradable polymer; a middle layer comprising mTOR inhibitor, and at least one biodegradable polymer; and a top layer selected from the group consisting of hydrophilic polymer, and combination of hydrophilic polymer and antioxidant to obtain a coated implantable medical device; wherein the solution concentration of mTOR inhibitor and the polymer in the base layer and the middle layer is in the range of 0.01 to 1% (w/v); wherein the solution concentration of the polymer and the antioxidant in the top layer is in the range of 0.01 to 5% (w/v).

The organic solvent used in the present disclosure is selected from the group consisting of dichloromethane, chloroform, hexafluoro isopropanol combinations thereof.

The present disclosure further relates to a method of preparing a coated implantable medical device, the process comprising: coating the bare metallic medical device with blend of mTOR inhibitor with biodegradable polymers in multiple layers. mTOR inhibitor with blend of biodegradable polymers are incorporated in the base and middle layer while the top layer selected from the group consisting of hydrophilic polymer, and combination of hydrophilic polymer and antioxidant are coated to protect the underneath layers.

The release of mTOR inhibitor from the mTOR eluting medical device is diffusion controlled in which the mTOR inhibitor is eluted virtually at constant rate from the medical device surface which is available across the vessel wall. The release was possible by distributing the total mTOR inhibitor content between two layers having different mTOR inhibitor to polymer ratio. Biodegradable polymers within the polymeric blend and their concentrations are selected on the basis of required mTOR inhibitor release and coating surface integrity.

The diffusion controlled release rate in controlled by adding one or more drug-mTOR layer. The mTOR inhibitor release is obtained at day 1 is in the range of 10-30% of the total mTOR inhibitor coated on the implantable medical device. The average 20% mTOR inhibitor release is obtained at day 1.

The mTOR release from the two layers, base and middle layer, provides precise control over mTOR eluting medical device. Higher mTOR inhibitor release at initial intervals is characteristics of thin film mTOR inhibitor releasing coating. Such type of coating is not favorable for mTOR eluting medical device as higher mTOR release may exhibit adverse effects locally. At longer time duration, mTOR inhibitor within coating layer exhaust when there is still requirement of it to prevent smooth muscle cell proliferation which is primary mechanism of restenosis process. The mTOR eluting medical device of the present disclosure provides an average of 20% mTOR (10% to 30% range) inhibitor release in biological serum at day 1.

The coated medical devices were packed with nitrogen.

The conformal coating process, which includes abluminal and luminal coating) is done on the medical device surface. The coating on the medical device can be done either by spraying the medical device with a polymer/mTOR inhibitor, or by dipping the medical device into a polymer/mTOR inhibitor solution, as well as the desired character of the coating itself. The preferred coating used in the present disclosure is by spray coating technology. It should "coat the stent smoothly and evenly" and "provide a uniform, predictable, prolonged release of the mTOR inhibitor." Surface coatings, however, can provide little actual control over the release kinetics of beneficial agents.

EXAMPLES

The disclosure will now be illustrated with working examples, which is intended to illustrate the working of disclosure and not intended to take restrictively to imply any limitations on the scope of the present disclosure.

Example 1

Spray Coating Technology and Coating Process

Stents were coated with mTOR inhibitor-polymer solution using air brush technique. This technique was modified to provide conformal coating around entire stent surface. The coating solution was fed to the feed cup provided on the spray nozzle which flows to the nozzle under gravity. Solution was atomized by means of pressurized inert gas flowing through the nozzle. The pressure drop around the nozzle atomizes the solution which was carried away in inert gas stream to the stent surface. The spray nozzle was provided the oscillating motion in vertical plane while stent was rotated on its axis. mTOR inhibitor-polymer solution was sprayed till desired amount of mTOR inhibitor-polymer weight was achieved. After coating process, stents are vacuum dried to remove the traces of organic solvent.

Example 2

Stent Coating Process

Coating solution for base layer was prepared by blending of everolimus with biodegradable polymers (PLCL and PLLA) in a ratio of 15:85 by weight in dichloromethane with total solid concentration of 0.3% (w/v). The PLCL and PLLA in base layer solution are blended in a ratio of 95:5 by weight. Similarly coating solution for middle layer was prepared by blending of everolimus with biodegradable polymers (PLCL and PLLA) in a ratio of 23:77 by weight in dichloromethane with total solid concentration of 0.25% (w/v). The PLCL and PLLA in middle layer solution are blended in a ratio of 85:15 by weight. Coating solution of top layer was prepared by mixing of polyvinyl pyrrolidone in dichloromethane at concentration of 0.125% (w/v). Alpha tocopherol was added in the top layer solution at a concentration of 1% (w/w) with respect to the total amount of drug taken in base layer and middle layer solutions.

12 mm Flexinnium Co—Cr Stents were pre-cleaned to remove any impurities on surface using dichloromethane. Pre-cleaned stents were then accurately weighed before coating. Base layer was coated on the stents to achieve 190 µg precise amount of everolimus and polymers. Base layer coated stent is vacuum dried at level of 400 mm Hg for about 1 hour for complete removal of DCM. Then after middle layer solution (prepared by mixing everolimus and PLCL and PLLA in the ratio of 23:77 by weight) was spray coated on stent to achieve 38 µg. predefined amount of everolimus and PLCL and PLLA. The middle layer coating was also vacuum dried at parameters mentioned previously. Stent was coated then with top layer coating solution and vacuum dried. The amount of PVP and anti-oxidant in top layer is 25 µg. Coated stent was analyzed by High Performance Liquid Chromatography for total drug content as well as in-vitro release of m-TOR.

TABLE

Composition of Coating Layers (Example-2)

| Layer | Material | Drug/Polymer ratio |
|---|---|---|
| Base Layer | Everolimus, Poly L-Lactide-co-Caprolactone | 15/85 |
| Middle Layer | Everolimus, Poly L-Lactide, Poly L-Lactide-co-Caprolactone | 23/77 |
| Top Layer | Polyvinyl Pyrrolidone, DL alpha tocopherol acetate | 0/100 |

Example 3

Coating of Stent in Two Layers with Drug Dose of 1.0 µg/mm$^2$

The stent was coated with two different layers by air atomized spray coating technology. Solution for base layer and top layer was prepared by dissolving the drug and biodegradable polymer in pre-definite composition as mentioned in Table-1. The solution was sprayed with pre-definite flow rate (0.15-0.4 ml/min) on a stent. The stent was vacuum dried for 30 min to 180 min after coating of individual layer to ensure complete evaporation of solvent. Gravimetric weight of stent was measured accurately after coating of each layer. The stent was EtO sterilized and analyzed for drug loading and in-vitro drug release. Drug release study was performed by incubating the stents in biological serum at 37° C. and analyzing the drug release at various time intervals using HPLC. Drug release results of the stents are represented in Table-2 and graphically in FIG. 1.

TABLE 1

Composition of Coating Layers (Example-3)

| Layer | Material | Drug/Polymer ratio |
|---|---|---|
| Base Layer | Everolimus, Poly L-Lactide-co-Caprolactone | 18/82 |
| Top Layer | Polyvinyl Pyrrolidone | 0/100 |

TABLE 2

In-vitro Drug Release Results of Stents (Example-3)

| Time | Cumulative drug release (%) | |
|---|---|---|
| (Days) | Predicted* | Actual |
| 0 | 0 | 0 |
| 1 | 10-30 | 25.12 |
| 7 | 45-65 | 62.20 |

*Predictive drug release profile is derived from the clinical outcomes of the various formulation studies till date; their limitations and requirement to fulfill clinical need.

From the results of drug release, it is revealed that drug release profile from two layer formulation is on higher side at later stage when compare with predicted drug release. To match the acceptance criteria, three layer coating composition is developed.

Example 4

Coating of Stent in Three Layers with Drug Dose of 1.0 mg/mm$^2$

Figure 2:
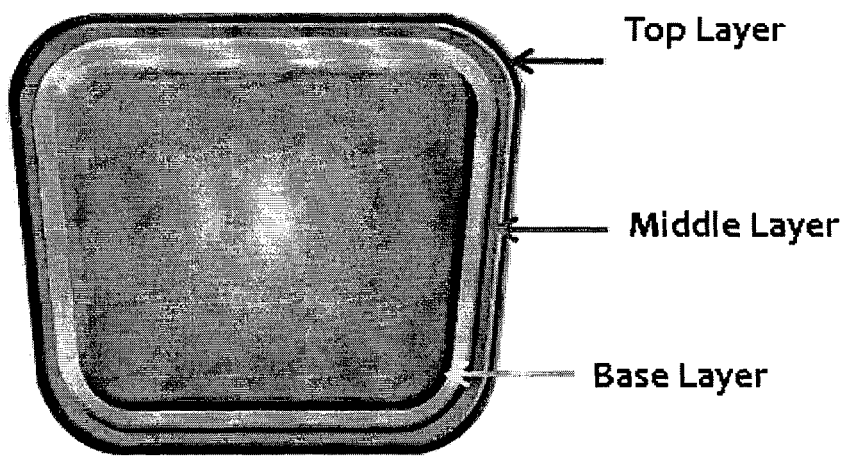
FIG. 2 illustrates the schematic diagram of three layer coating on stent.
Figure 3:
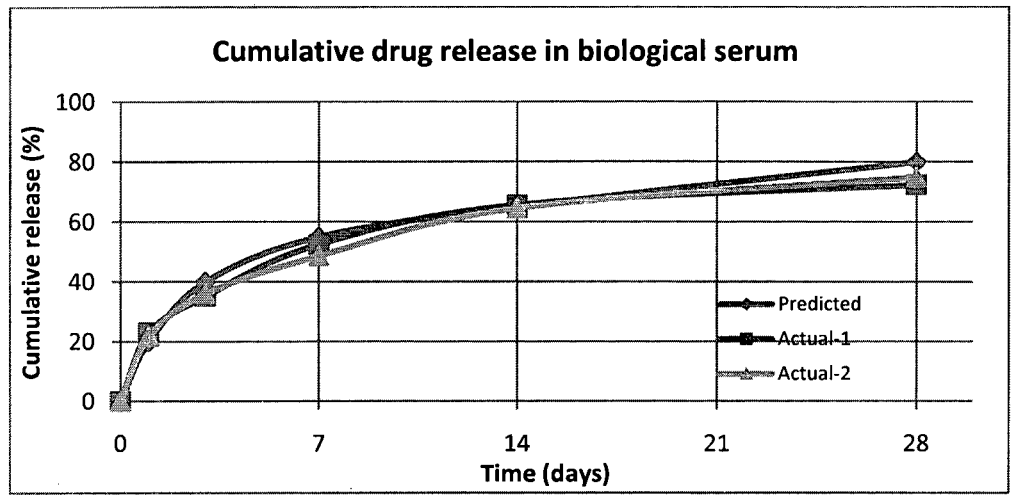
FIG. 3 illustrates the drug release profile of stents.

The stent was coated with three different layers by air atomized spray coating technology. Solution for base layer, middle layer and top layer was prepared by dissolving the drug and biodegradable polymers in pre-definite composition as mentioned in Table-3. The solution was sprayed with pre-definite flow rate (0.15-0.4 ml/min) on a stent. The stent was vacuum dried after coating of individual layer to ensure complete evaporation of solvent. Schematic of three layer coating was presented in FIG. 2. Gravimetric weight of the stent was measured accurately after coating of each layer. The stent was EtO sterilized and analyzed for drug loading and in-vitro drug release. Drug release study was performed by incubating the stents in biological serum at 37° C. and analyzing the drug release at various time intervals using HPLC. Drug release results of the stents are represented in Table-4 and graphically in FIG. 3.

TABLE 3

Composition of Coating Layers (Example-4)

| Layer | Material | Drug/Polymer ratio |
|---|---|---|
| Base Layer | Everolimus, Poly L-Lactide, Poly L-Lactide-co-Caprolactone | 15/85 |
| Middle Layer | Everolimus, Poly L-Lactide, Poly L-Lactide-co-Caprolactone | 23/77 |
| Top Layer | Polyvinyl Pyrrolidone | 0/100 |

TABLE 4

In-vitro Drug Release Results of Stents (Example-4)

| Time | Cumulative drug release (%) | | |
|---|---|---|---|
| (Days) | Predicted | Experiment 1 | Experiment 2 |
| 0 | 0 | 0 | 0 |
| 1 | 10-30 | 22.95 | 21.73 |
| 3 | 30-50 | 35.18 | 35.94 |
| 7 | 45-65 | 52.54 | 48.65 |
| 14 | 55-75 | 65.64 | 64.60 |
| 28 | 70-90 | 72.39 | 74.99 |

\* Experiment 1 was conducted once and Experiment 2 is a repeat study of Experiment 1. We can change the nomenclature if required to avoid confusion.

Drug release results of three layer composition evaluated for two different sets of stents are matching the predicted drug release profile.

Example 5

Coating of Stent in Two Layers with Drug Dose of 1.4 μg/mm$^2$

Figure 4:
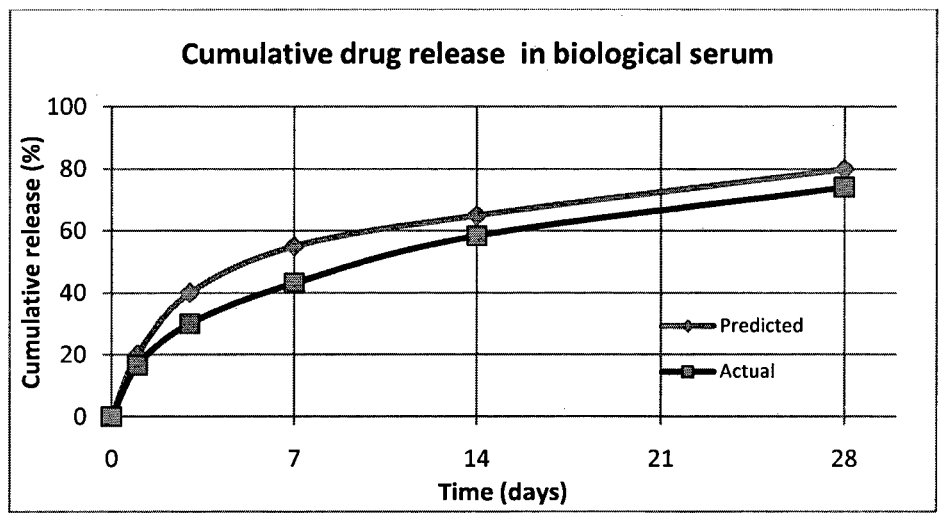
FIG. 4 illustrates the drug release profile of stents.

The stents was coated with two different layers by air atomized spray coating technology. Solution for base layer and top layer was prepared by dissolving the drug and biodegradable polymer in pre-definite composition as mentioned in Table-5. The solution for base layer was sprayed with pre-definite flow rate (0.15-0.4 ml/min) on a stent. The stent was vacuum dried after coating of individual layer to ensure complete evaporation of solvent. Gravimetric weight of stent was measured accurately after coating of each layer. The stent was EtO sterilized and analyzed for drug loading and in-vitro drug release. Drug release study was performed by incubating the stents in biological serum at 37° C. and analyzing the drug release at various time intervals using HPLC. Drug release results of the stents are represented in Table-6 and FIG. 4.

TABLE 5

Composition of Coating Layers (Example-5)

| Layer | Material | Drug/Polymer ratio |
|---|---|---|
| Base Layer | Everolimus, Poly L-Lactide-co-Caprolactone | 18/82 |
| Top Layer | Polyvinyl Pyrrolidone | 0/100 |

TABLE 6

In-vitro Drug Release Results of Stents (Example-5)

| Time | Cumulative drug release | |
|---|---|---|
| (Days) | Predicted | Actual |
| 0 | 0 | 0 |
| 1 | 10-30 | 16.51 |
| 3 | 30-50 | 30.08 |
| 7 | 45-65 | 43.13 |
| 14 | 55-75 | 58.44 |
| 28 | 70-90 | 74.16 |

From the results of drug release, it is revealed that drug release profile from two layer formulation doesn't match with the predicted drug release. To match the acceptance criteria, three layer coating composition is developed.

Example 6

Coating of Stent in Three Layers with Drug Dose of 1.4 μg/mm$^2$

Figure 5:
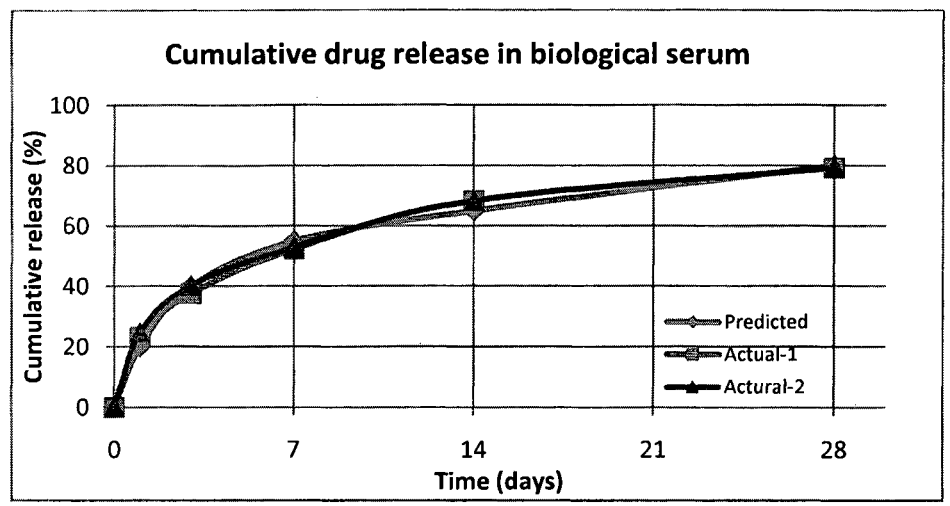

The stents was coated with three different layers by air atomized spray coating technology. Solution for base layer, middle layer and top layer was prepared by dissolving the drug and biodegradable polymers in pre-definite composition as mentioned in Table-7. The solution of base layer was sprayed with pre-definite flow rate (0.15-0.4 ml/min) on a stent. The stent was vacuum dried after coating of individual layer to ensure complete evaporation of solvent. Schematic of three layer coating is presented in FIG. 2. Gravimetric weight of the stent was measured accurately after coating of each layer. The stent was EtO sterilized and analyzed for drug loading and in-vitro drug release. Drug release study was performed by incubating the stents in biological serum at 37° C. and analyzing the drug release at various time intervals using HPLC. Drug release results of the stents are represented in Table-8 and FIG. 5.

TABLE 7

Composition of Coating Layers (Example-6)

| Layer | Material | Drug/Polymer ratio |
|---|---|---|
| Base Layer | Everolimus, Poly L-Lactide-co-Caprolactone | 15/85 |
| Middle Layer | Everolimus, Poly L-Lactide, Poly L-Lactide-co-Caprolactone | 25/75 |

TABLE 7-continued

Composition of Coating Layers (Example-6)

| Layer | Material | Drug/Polymer ratio |
|---|---|---|
| Top Layer | Polyvinyl Pyrrolidone | 0/100 |

TABLE 8

In-vitro Drug Release Results of Stents (Example-6)

| Time (Days) | Cumulative drug release | | |
|---|---|---|---|
| | Predicted | Experiment 1 | Experiment 2 |
| 0 | 0 | 0 | 0 |
| 1 | 10-30 | 23.12 | 24.61 |
| 3 | 30-50 | 37.60 | 40.21 |
| 7 | 45-65 | 52.30 | 52.96 |
| 14 | 55-75 | 68.34 | 68.23 |
| 28 | 70-90 | 79.09 | 79.34 |

Experiment 2 was confirmation for Experiment 1. The process parameters and solution compositions were same in Experiment 1 and Experiment 2

Drug release results of three layer composition evaluated for two different sets of stents are match with the predicted drug release profile.

Example 7

Coating of Stent in Three Layers with Drug Dose of 1.4 µg/mm²

The stents was coated with three different layers by air atomized spray coating technology. Solution for base layer, middle layer and top layer was prepared by dissolving the drug, biodegradable polymers and antioxidant in pre-definite composition as mentioned in Table-9. The solution of base layer was sprayed with pre-definite flow rate (0.15-0.4 ml/min) on a stent. The stent was vacuum dried after coating of individual layer to ensure complete evaporation of solvent. Schematic of three layer coating is presented in FIG. 2. Gravimetric weight of the stent was measured accurately after coating of each layer. The samples were EtO sterilized and analyzed for drug loading and in-vitro drug release. Drug release study was performed by incubating the stents in buffer media simulating body conditions at 37° C. and analyzing the drug release at various time intervals using HPLC. Results of the stents are represented in Table-10.

TABLE 9

Composition of Coating Layers (Example-7)

| Layer | Material | Drug/Polymer ratio |
|---|---|---|
| Base Layer | Everolimus, Poly L-Lactide-co-Caprolactone | 15/85 |
| Middle Layer | Everolimus, Poly L-Lactide, Poly L-Lactide-co-Caprolactone | 25/75 |
| Top Layer | Polyvinyl Pyrrolidone, DL alpha tocopherol acetate | 0/100 |

TABLE 10

In-vitro Drug Release Results of Stents (Example-7)

| Time (hours) | Cumulative drug release (%) | |
|---|---|---|
| | Preferred drug release range | Results |
| 0 | 0 | 0 |
| 0.5 | 19-31 | 25.57 |
| 1.5 | 32-48 | 40.88 |
| 3.0 | 42-64 | 53.73 |
| 6.0 | 52-78 | 68.15 |
| 24 | ≥80 | 89.65 |

Advantages

The previously described versions of the subject matter and its equivalent thereof have many advantages, including those which are described below.

The present disclosure provides a mTOR inhibitor eluting medical device having conformal coating i.e. has a protection against moisture, dust, chemicals, and temperature.

The mTOR inhibitor eluting medical device of the present disclosure provides an average of 20% (10 to 30% range) mTOR inhibitor release in biological serum at day 1.

The mTOR inhibitor eluting medical device of the present disclosure has been prepared by coating the bare metallic stent with blend of Everolimus with biodegradable polymers in multiple layers. Drug is incorporated in base and middle layer while top layer is coated to protect the underneath layers. This top layer does not contain any drug.

Release of Everolimus from the mTOR inhibitor eluting medical device of the present disclosure is diffusion controlled in which drug is eluted virtually at constant rate from stent surface which is available across the vessel wall. Such release was possible by distributing the total drug content between two layers having different drug to polymer ratio. Biodegradable polymers within polymeric blend and their concentrations are selected on the basis of required drug release and coating surface integrity.

Drug release from two layers provides precise control over drug elution from stent. Higher drug release at initial intervals is typical characteristics of thin film drug releasing coating. Such type of coating is not favorable for drug eluting stents as higher drug release may exhibit adverse effects locally. Also at longer time duration, drug within coating layer exhausts when there is still requirement of it to prevent smooth muscle cell proliferation which is primary mechanism of restenosis. The mTOR inhibitor eluting medical device of the present disclosure is designed considering this fact and provides average of 20% drug release in biological serum.

The mTOR inhibitor eluting medical device of the present disclosure has incorporated alpha tocopherol acetate within the top layer along to protect Everolimus drug against oxidative degradation, thus improving the stability of Everolimus.

Although the subject matter has been described in considerable detail with reference to certain preferred embodiments thereof, other embodiments are possible. As such, the spirit and scope of the appended claims should not be limited to the description of the preferred embodiment contained therein.

We claim:

1. A coated implantable medical device, consisting of:
   an implantable medical device selected from the group consisting of a stent, a guide wire, a heart valve, a catheter, a vena cava filter, a vascular graft, a stent graft and combinations thereof;
   a base layer on said implantable medical device consisting of one or more mTOR inhibitors, one or more biodegradable polymers and, optionally, one or more antioxidants, said one or more mTOR inhibitors dispersed in said one or more biodegradable polymers and selected from the group consisting of everolimus, pimecrolimus, tacrolimus, zotarolimus, biolimus, rapamysin, and mixtures thereof and wherein a weight ratio of said one or more mTOR inhibitors to said one or more biodegradable polymers is in a range of from 10:90 to 30:70;
   a middle layer on said implantable medical device consisting of one or more mTOR inhibitors, one or more biodegradable polymers and, optionally, one or more antioxidants, said one or more mTOR inhibitors dispersed in said one or more biodegradable polymers and selected from the group consisting of everolimus, pimecrolimus, tacrolimus, zotarolimus, biolimus, rapamysin, and mixtures thereof and wherein a weight ratio of said one or more mTOR inhibitors to said one or more biodegradable polymers is in a range of from 15:85 to 40:60 and wherein in said middle layer said weight ratio of said one or more mTOR inhibitors is greater than in said base layer; and
   a top layer on said medical device selected from the group consisting of one or more hydrophilic polymers, and a combination of one or more hydrophilic polymers with one or more antioxidants, the top layer being mTOR inhibitor-free, wherein a total antioxidant concentration of the one or more antioxidants in the top layer varies from 0.5 weight percent to 10 weight percent with respect to a total mTOR inhibitor concentration over said medical device;
   wherein a total mTOR inhibitor concentration over said medical device is in the range of from 0.7 to 3.00 μg/mm$^2$ and wherein said base layer has a higher total amount of said one or more mTOR inhibitors than said middle layer, and wherein from 10 to 30% of the total amount of said one or more mTOR inhibitors is released from said medical device in the first 24 hours after use with the remainder of said mTOR inhibitor being released from said medical device over a period of time of 28 days or longer; and
   wherein said one or more biodegradable polymers in said base and said middle layer are selected from the group consisting of poly(L-lactide-co-caprolactone) (PLCL), poly L-lactide (PLLA), poly dl lactide (PDLLA), poly dl lactide-co-glycolide (PLGA), poly dl lactide-co-caprolactone (PLLCL), and combinations thereof.

2. The coated implantable medical device as claimed in claim 1, wherein each of said middle layer and said base layer further comprise an antioxidant.

3. The coated implantable medical device as claimed in claim 1, wherein said one or more antioxidants is selected from the group consisting of tocopherol acetate, Vitamin E, butylated hydroxyl toluene (BHT) and combinations thereof.

4. The coated implantable medical device as claimed in claim 1, wherein said one or more hydrophilic polymers is selected from the group consisting of pyrrolidone polymers.

5. The coated implantable medical device as claimed in claim 1, wherein:
   the base layer comprises everolimus and a blend of poly(L-lactide-co-caprolactone) (PLCL) and poly L-lactide (PLLA);
   the middle layer comprises everolimus and a blend of poly(L-lactide-co-caprolactone) (PLCL) and poly L-lactide (PLLA); and
   the one or more hydrophilic polymers includes polyvinyl pyrrolidone and the one or more antioxidants includes tocopherol acetate.

6. A method of preparing a coated implantable medical device as claimed in claim 1, the coating process comprising:
   pre-cleaning a medical device selected from the group consisting of a stent, a guide wire, a heart valve, a catheter, a vena cava filter, a vascular graft, a stent graft and combinations thereof using an organic solvent to obtain a cleaned medical device; and
   coating the cleaned medical device with the base layer;
   coating the base layer with the middle layer; and
   coating the middle layer with the top layer to obtain a coated implantable medical device;
   wherein the one or more mTOR inhibitors and the one or more biodegradable polymers in the base layer and the middle layer has a solution concentration in the range of 0.01 to 1% (w/v).

7. The method as claimed in claim 6, wherein the one or more hydrophilic polymers and the one or more antioxidants in the top layer has a solution concentration in the range of from 0.01 to 5% (w/v).

8. The method as claimed in claim 6, wherein the organic solvent is selected from the group consisting of dichloromethane, chloroform, hexafluoro isopropanol, and combinations thereof.

9. The coated implantable medical device as claimed in claim 6, wherein the coating process is done on an abluminal surface, a luminal surface and side walls of the medical device.

10. The coated implantable medical device as claimed in claim 1, wherein said device is a stent.

11. The coated implantable medical device as claimed in claim 10, wherein said one or more mTOR inhibitors is everolimus.

12. The coated implantable medical device as claimed in claim 11, wherein said one or more biodegradable polymers is selected from the group consisting of poly L-lactide (PLLA), poly(L-lactide-co-caprolactone (PLCL), and a mixture thereof.

13. The coated implantable medical device as claimed in claim 12, wherein said one or more antioxidants is tocopherol acetate.

14. The coated implantable medical device as claimed in claim 13, wherein said one or more hydrophilic polymers is polyvinyl pyrrolidone.

15. The coated implantable medical device as claimed in claim 1, wherein the top layer does not contain any drug.

16. The coated implantable medical device as claimed in claim 1, wherein:
   30%-50% of said one or more mTOR inhibitors is released from said medical device in the first 3 days,
   45%-65% of said one or more mTOR inhibitors is released from said medical device in the first 7 days, and
   55%-75% of said one or more mTOR inhibitors is released from said medical device in the first 14 days.

17. The coated implantable medical device as claimed in claim 1, wherein the at least one biodegradable polymer in the base layer and middle layer has a weight ratio in the range from 10% to 40% based on the mTOR inhibitor weight.

18. The coated implantable medical device as claimed in claim 1, wherein said one or more biodegradable polymers in said base layer and said middle layer comprises a mixture of poly L-lactide and poly(L-lactide-co-caprolactone) each having a weight ratio in the range from 10% to 40% based on said mTOR inhibitor weight.

\* \* \* \* \*